(12) United States Patent
Demmer et al.

(10) Patent No.: US 10,100,294 B2
(45) Date of Patent: Oct. 16, 2018

(54) PROCESS FOR THE SEPARATION OF A MIXTURE OF A PROTEIN AND ITS REACTION PRODUCT WITH A POLYALKYLENE GLYCOL

(75) Inventors: Wolfgang Demmer, Goettingen (DE); Louis Villain, Hannover (DE); Hans-Heinrich Hoerl, Bovenden (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 752 days.

(21) Appl. No.: 14/117,782

(22) PCT Filed: Mar. 21, 2012

(86) PCT No.: PCT/EP2012/001230
§ 371 (c)(1),
(2), (4) Date: Nov. 14, 2013

(87) PCT Pub. No.: WO2012/156000
PCT Pub. Date: Nov. 22, 2012

(65) Prior Publication Data
US 2015/0140637 A1    May 21, 2015

(30) Foreign Application Priority Data

May 19, 2011   (DE) .................. 10 2011 101 995

(51) Int. Cl.
| | | |
|---|---|---|
| *C12N 9/26* | (2006.01) | |
| *C12N 9/36* | (2006.01) | |
| *C07K 1/16* | (2006.01) | |
| *A61K 47/60* | (2017.01) | |

(52) U.S. Cl.
CPC ............ *C12N 9/2462* (2013.01); *A61K 47/60* (2017.08); *C07K 1/16* (2013.01)

(58) Field of Classification Search
None
See application file for complete search history.

(56) References Cited

U.S. PATENT DOCUMENTS

| | | |
|---|---|---|
| 2005/0089952 A1 | 4/2005 | Chavez et al. |
| 2011/0110882 A1* | 5/2011 | Preiss-Bloom ........ A61K 8/042 |
| | | 424/78.27 |
| 2011/0163029 A1 | 7/2011 | Faber et al. |

FOREIGN PATENT DOCUMENTS

| | | |
|---|---|---|
| DE | 10 2008 018 732 | 10/2009 |
| WO | 2005/029065 | 3/2005 |
| WO | 2006/011839 | 2/2006 |
| WO | 2007056191 | 5/2007 |
| WO | 2008057683 | 5/2008 |
| WO | 2008/154639 | 12/2008 |
| WO | WO 2009127287 | * 10/2009 |

OTHER PUBLICATIONS

Corning filter selection guide 2005 (http://web.archive.org/web/20050218062427/http://www.cultek.com/pdf/t_filterselectionguide.pdf).*
Fee et al.—"PEG-proteins: Reaction engineering and separation issues"—Chemical Engineering Science 61 (2006) pp. 924-939.
Molek et al.—"Separation of PEGylated a-Lactalbumin from Unreacted Precursors and Byproducts Using Ultrafiltration"—Biotechnol. Prog. 2007, 23, pp. 1417-1424.
International Search Report dated May 9, 2012.

* cited by examiner

*Primary Examiner* — Christopher R Tate
*Assistant Examiner* — Douglas F White
(74) *Attorney, Agent, or Firm* — Gerald E. Hespos; Michael J. Porco; Matthew T. Hespos

(57) ABSTRACT

The present invention relates to a process for the separation of a mixture of a protein and its reaction product with a polyalkylene glycol, comprising the steps: a) providing a mixture comprising the protein and the reaction product in a fluid, b) bringing the mixture of step a) into contact with a microporous cellulose acetate membrane with adsorption of the reaction product onto the cellulose acetate membrane, the protein not becoming adsorbed onto the cellulose acetate membrane, c) removal of the protein from the cellulose acetate membrane, and d) desorbing the reaction product from the cellulose acetate membrane, the reaction product being selected from the group comprising the protein which is mono- or polyfunctionalized by the polyalkylene glycol, or mixtures thereof.

11 Claims, 5 Drawing Sheets

PROCESS FOR THE SEPARATION OF A MIXTURE OF A PROTEIN AND ITS REACTION PRODUCT WITH A POLYALKYLENE GLYCOL

BACKGROUND

1. Field of the Invention

The present invention relates to a process for the separation of a mixture of a protein and its reaction product with a polyalkylene glycol.

2. Description of the Related Art

When using therapeutic proteins in medicine, the proteins are frequently functionalized with a polyethylene glycol to prolong the biological half-life and thus the duration of action after the uptake into the patient's bloodstream. A frequently used synonym for a protein functionalized with a polyethylene glycol unit is the expression mono-, di-, or poly-"pegylated" protein where the protein molecule is optionally functionalized with one, two or more polyethylene glycol polymer chains. Owing to their greater hydrodynamic radius, pegylated proteins are eliminated more slowly via the kidneys than the corresponding nonpegylated proteins. Furthermore, the pegylation reduces a side-effect of the protein as antigen, which is undesired for the patient.

Efficient processes for the rapid determination of the amount of a mono-, di- and/or polypegylated protein in a substance mixture are becoming increasingly important in medical and biopharmaceutical rapid analysis because these processes provide within a short time reliable findings on the quantitative composition of such mixtures and on the degree of pegylation of the proteins present therein.

In recent years, a variety of processes have become established by means of which proteins, via their amino groups, can be reacted with chemically activated polyalkylene glycols, for example, polyalkylene glycols including aldehyde groups, to give Schiff's bases (imines), in which processes the imine groups of the protein are subsequently reduced to give pegylated amino groups. Depending on the number of amino groups of a protein which are involved in this reaction sequence with a polyethylene glycol, a mono-, di- or poly-"pegylated" protein results.

WO 2007/056191 A2 discloses a process for the purification of nucleotides which include a glycine unit whose amino group is functionalized with a polyethylene glycol unit. The monopegylated nucleotide can be separated from the unreacted pegylating reagent by a combination of membrane filtration (reverse osmosis or nanofiltration), size exclusion chromatography with polyacrylamide resins and ion-exchange chromatography with Q-Sepharose®. This document does not provide processes for the separation of mixtures which include mono-, di- and polypegylated nucleotides and/or proteins into the individual components.

WO 2008/154639 A2 discloses a process for the purification of monopegylated nucleotides in high yield and purity, where the monopegylated nucleotide is separated from the nonpegylated nucleotide and the unreacted pegylating reagent by anion-exchange chromatography using Q-Sepharose® gels, Mustang®-Q or Sartobind®-Q membrane adsorbers, followed by ultrafiltration and/or tangential flow filtration. Again, this document does not provide processes for the separation of mixtures which include mono-, di- and polypegylated nucleotides and/or proteins into the individual components.

WO 2006/011839 A1 discloses a process for the purification of a mono- or polypegylated 30 kDa protein which is not specified in more detail, using a chromatography gel based on a crosslinked copolymer of allyl dextran and N,N-methylenebisacrylamide, such as, for example, Sephacryl® S 500. Ion-exchanging or hydrophobic groups or affinity groups or metal-chelating groups are immobilized on the surface of the chromatography gel. The process allows the monopegylated protein to be separated from the polypegylated protein.

WO 2005/029065 A1 discloses chromatography matrices which are composed of crosslinked agarose on whose surface polyacrylic-acid-based polymer chains are fixed in place. Using these chromatography matrices, monopegylated proteins are separated from the starting materials of a pegylation reaction, i.e. from the unreacted pegylating reagent and from the nonpegylated proteins. It is the proton-donating carboxylic acid functions of the polyacrylic acid polymer chains which are essential to the success of the process. It has been found for the chromatography matrices disclosed in WO 2005/029065 A1 that, for a gradient elution, the binding interaction between the matrix and the components of the reaction mixture decreases in the order pegylating reagent>monopegylated component>nonpegylated component. As in the previously mentioned documents, this document, too, does not disclose any process for the separation of mono- and polypegylated-protein-containing mixtures into the individual components.

US 2005/0089952 A1 discloses the removal of a nonpegylated protein, for example lysozyme, from its mono- and polypegylated reaction products using membranes of polyether sulfone or regenerated cellulose in a tangential flow or diafiltration process. The decisive factor for the removal of the nonpegylated protein from the pegylated components is a molecular weight cut-off value (MWCO value) of the membranes of at least 30 kDa. Under this condition, the nonpegylated lysozyme passes across the membrane in the permeate stream while up to 97-99.2% of the pegylated lysozyme species are retained by the membrane. The aim of the separation process disclosed in US 2005/0089952 A1 is the efficient removal to the highest possible quantitative degree of the nonpegylated protein from the mono- or polypegylated protein species so that the nonpegylated protein may be recovered and recirculated into the reaction vessel for pegylation. Accordingly, this document, too, does not contain any disclosure as to how a mixture of mono- and polypegylated proteins can be separated into these species, using the abovementioned membranes.

In Biotechnol. Prog. 2007 (23), 1417-1424, J. R. Molek and L. Zydney disclose the removal of pegylated lactalbumin from nonpegylated lactalbumin and from further by-products by means of neutral or sulfonic-acid-group-functionalized ultrafiltration membranes based on regenerated cellulose and having an MWCO value of 30 or 100 kDa, respectively.

In their review paper from Chemical Engineering Science, 61, 2006, 924-939, C. J. Fee et al. disclose various separation methods, including size exclusion, affinity, hydrophobe interaction, cation exchange, metal chelate, reversed-phase and anion exchange chromatography methods for removing pegylated therapeutic proteins from their nonpegylated protein starting materials.

SUMMARY OF THE INVENTION

The present invention is based on the object of providing a process for the separation of mixtures of a protein and its reaction products which are mono- or poly-functionalized by polyalkylene glycol, which process makes it possible to individually remove not only the protein, but also the polyalkylene-glycol-functionalized proteins in an efficient and financially advantageous manner and which simultaneously makes it possible to determine rapidly and in a financially advantageous manner the quantitative ratios in which the protein and its reaction products are present in the mixture.

This object is achieved by a process for the separation of the abovementioned protein mixtures which meets the abovementioned demands. In this context, it has surprisingly been found that it is possible to separate mixtures of a protein and its polyalkylene-glycol-functionalized reaction products into the individual components by using a microporous cellulose acetate membrane.

Accordingly, the invention relates to a process for the separation of a mixture of a protein and its reaction product with a polyalkylene glycol, comprising the steps:
a) providing a mixture comprising the protein and the reaction product in a fluid,
b) bringing the mixture of step a) into contact with a microporous cellulose acetate membrane with adsorption of the reaction product onto the cellulose acetate membrane, the protein not becoming adsorbed onto the cellulose acetate membrane,
c) removing the protein from the cellulose acetate membrane, and
d) desorbing the reaction product from the cellulose acetate membrane, the reaction product being selected from the group comprising the protein which is mono- or polyfunctionalized by the polyalkylene glycol, or mixtures thereof.

In accordance with the invention, the expression "polyalkylene glycol" comprises polyethers of the general formula HO—[R—O-]nH, where the alkylene group R is a divalent radical which has two hydrogen atoms fewer at two different C atoms than the basic alkane H—R—H, and where n is a natural number of two or greater. The alkylene group R may include hydrogen atoms, alkyl radicals and/or aryl radicals as substituents, it being possible for the alkyl or aryl radicals, in turn, to include further optional substituents, for example functional groups with heteroatoms. In accordance with the invention, the polyalkylene glycol may be a linear or branched polyether.

For the purposes of the present invention, a "protein" comprises any oligo- or polypeptide and higher-level primary, secondary or tertiary structures of a polypeptide which can be reacted with a polyalkylene glycol. In accordance with the invention, a "protein" is also understood as meaning aggregates of at least two of the abovementioned proteins.

The expression "reaction product" of a protein with a polyalkylene glycol comprises the direct or indirect reaction product of a functional reactive group of the protein with a complementary functional group of the polyalkylene glycol. In accordance with the invention, the abovementioned reaction product is understood as meaning, in particular, a product which is the result of the reaction of amino groups of the protein with aldehyde groups which can be introduced into the polyalkylene glycol by oxidation of —CH—OH— groups. This reaction first generates imines ("Schiff bases") which can be reacted in a subsequent step, for example, by reduction, to give amine groups of the protein which are functionalized by a polyether substituent.

Depending on the number of amine groups present in the protein and which are capable of reacting with complementary functional groups of the polyalkylene glycol, the resulting reaction product is a protein which only includes one amine group which is functionalized by a polyether substituent, this protein being a "protein which is monofunctionalized by the polyalkylene glycol" in accordance with the invention, or it results in a protein which includes two or more amine groups which are functionalized by a polyether substituent, this protein being a "protein which is polyfunctionalized by the polyalkylene glycol".

In accordance with the invention, a "mixture of a protein and its reaction product with a polyalkylene glycol" is understood as meaning a mixture of the protein and at least one of its abovementioned reaction products which are mono- or polyfunctionalized by a polyalkylene ether substituent.

To carry out the process according to the invention, it is preferred to employ, by way of polyalkylene glycol, a polyethylene glycol with a mean molecular weight of from 5 to 30 kDa.

Especially preferred in accordance with the invention are polyethylene glycols with activated aldehyde groups which can be reacted with free amine groups of the protein to give imines, which, in turn, can subsequently be reduced to amine groups which are mono- or polyfunctionalized by a polyethylene ether substituent. These proteins which are functionalized by what is known as a "pegylation" are hereinbelow synonymously also referred to as mono-, di-, tri- or multipegylated proteins. Processes for the pegylation of the amino groups of proteins have been described by M. R. Sherman et al. in "Conjugation of High-molecular Weight Poly(ethylene glycol) to Cytokines: Granulocyte-Macrophage Colony-stimulating Factors as Model Substrates" in the monograph "Poly (ethylene glycol) Chemistry and Biological Applications", ACS Symposium Series 680, editor: J. M. Harris, S. Zalipsky, American Chemical Society 1997, pp. 155-169, ISBN 0-8412-3537-6.

A "fluid" which is suitable in accordance with the invention is any liquid compatible with the protein and its reaction product and in which the protein and its reaction product can be provided as a mixture, i.e. in particular aqueous solutions of (in)organic salts to which optionally at least one alkanol may be admixed.

Within the scope of the present invention, the expression "microporous cellulose acetate membrane" refers to cellulose acetate membranes with a pore size of from 0.1 to 15 µm, preferably 0.1 to 5 µm and more preferably 0.2 to 0.45 µm. The pore size may be determined in what is known as a "capillary flow porometry test" (capillary flow porometer 6.0, CAPWIN Software System, Porous Materials Inc.). The microporous cellulose acetate membrane may be present in any form which is suitable for bringing the inner and outer surfaces of the membrane into contact with the mixture of the protein and its reaction product with a polyalkylene glycol. For example, the microporous cellulose acetate membrane may be integrated into a membrane adsorber module. Suitable membrane adsorber modules are disclosed, for example, in DE 102 36 664 A1.

In a further preferred embodiment of the invention, the cellulose acetate membrane is reinforced by a nonwoven or woven fabric so as to increase the mechanical strength of the membrane.

In accordance with a further preferred embodiment of the invention, the cellulose acetate membrane is composed of cellulose monoacetate, cellulose diacetate, cellulose triacetate or mixtures of these.

In accordance with a preferred embodiment of the process according to the invention, the reaction product of the protein with the polyalkylene glycol is a mixture which comprises the protein which is mono- and polyfunctionalized by the polyalkylene glycol and wherein, in step d), the polyalkylene-glycol-functionalized proteins are desorbed with an eluent from the cellulose acetate membrane individually, one after the other.

The eluent used in step d) is preferably an aqueous solution of an inorganic ammonium, alkali metal or alkaline earth metal salt, and/or of an ammonium, alkali metal or alkaline earth metal salt of an organic mono-, di-, or tricarboxylic acid, the polyalkylene-glycol-functionalized proteins being desorbed in step d) in an increasing concentration gradient of the eluent, with the salt concentration decreasing.

Desorption of the polyalkylene-glycol-functionalized proteins in an increasing concentration gradient is hereinbelow understood as meaning that the concentration of the salt(s) in the aqueous solution of the eluent is reduced as a function of the duration of the elution following a specific concentration/time function. Especially preferred in accordance with the invention is a linear reduction of the salt concentration, or a reduction of the salt concentration in the form of a step profile.

Inorganic ammonium, alkali metal or alkaline earth metal salts which have proven themselves are, in particular, salts from the group of the halides, sulfates or phosphates, while those which are preferred among the ammonium, alkali metal or alkaline-earth metal salts of the abovementioned mono-, di- or tricarboxylic acids are salts of formic acid, acetic acid, caproic acid, glycolic acid, lactic acid, malic acid, tartaric acid, fumaric acid, maleic acid, succinic acid, oxalic acid, malonic acid, ascorbic acid, glucuronic acid, alpha-ketoglutaric acid, (iso)citric acid, triallyl or aconitic acid.

A protein which is especially preferred for the process according to the invention is one that is selected from the group comprising immunoglobulins, insulins, interferons, albumins such as lactalbumin, ovalbumin, bovine serum albumin, myelopoietin, erythropoietin, trichosanthin, tumor necrosis factors or enzymes such as methioninase, ribonucleases, staphylokinases or lysozyme, or monoclonal or recombinant antibodies.

In an especially preferred embodiment of the process, the protein is lysozyme and the reaction product of the protein is a mixture composed of lysozyme which is mono-, di- and trifunctionalized by polyethylene glycol. In the abovementioned embodiment, it is possible to separate all four components by the process according to the invention, to isolate them and to determine their quantitative proportion of the pegylation product mixture.

The present invention is illustrated in greater detail with reference to the figures and with reference to the following, nonlimiting example.

EXAMPLE

Pegylation of Lysozyme

DETAILED DESCRIPTION OF THE PREFERRED EMBODIMENTS

Figure 1:
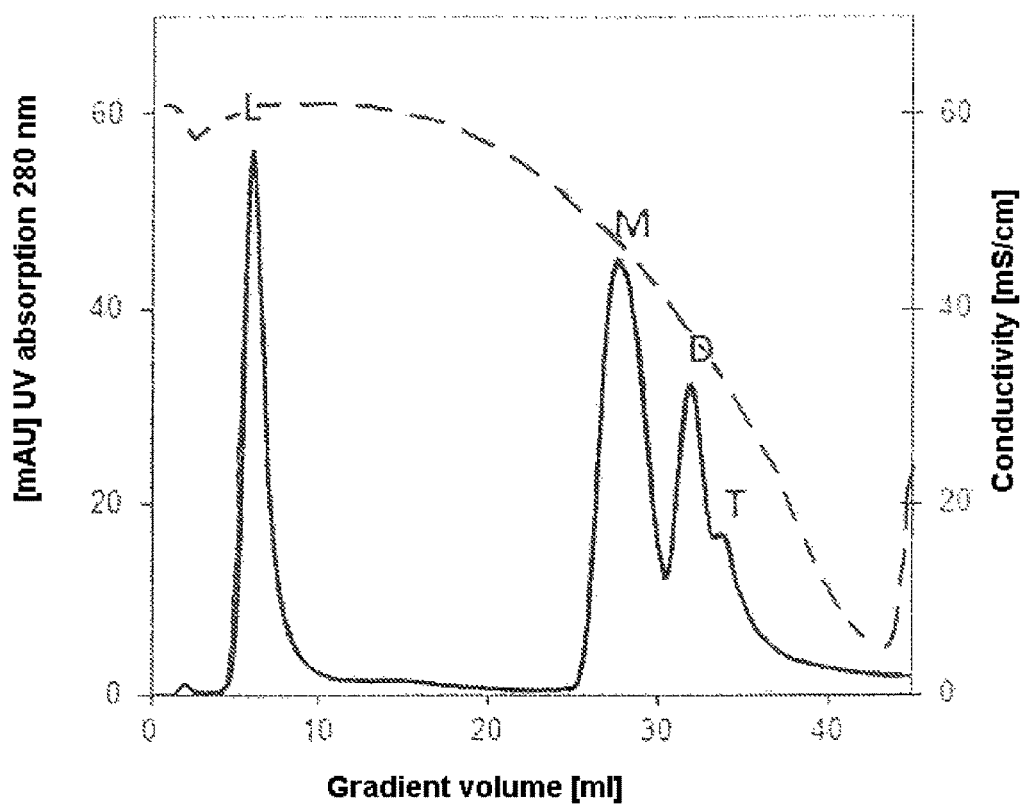
FIG. 1 a chromatogram of a reaction mixture from the reaction of lysozyme with 5-kDa polyethylene glycol during a gradient elution, the volume of the 0.20 μm cellulose acetate membrane being 1 ml.

The starting materials used for the pegylation were the polyethylene glycol SUNBRIGHT® ME-050AL with activated aldehyde groups and a mean molecular weight of 5000 Da (daltons) from NOF Europe, The Netherlands, Batch No. M83596, and lysozyme with a mean molecular weight of 14 700 Da from SIGMA Aldrich, Germany, Order No. L6876-100G, Batch No.: 088K1358, and sodium cyanoborohydride $NaCN(BH_3)$ from FLUKA Buchs, Switzerland, Order No. 71435, Batch No. 1259328. Lysozyme and the polyethylene glycol (PEG) were dissolved in each case in a 10 mmol/l citrate buffer (pH 8.0). Sodium cyanoborohydride was added to the lysozyme-containing solution. The reaction started at room temperature immediately after mixing the lysozyme- and $NaCN(BH_3)$-containing solution with the PEG-containing solution. The amounts employed were chosen such that the lysozyme concentration in the reaction mixture was 2 mg/ml and the quantitative ratio of PEG to lysozyme was 3:1. In one mixture, 200 mg of lysozyme, 140 mg of PEG and 200 mg of sodium cyanoborohydride were employed. The components were reacted at room temperature for 20 h and subsequently stored at 4° C. for 8 h. Thereafter, the mixture of the pegylation products and of the unreacted lysozyme was purified by strongly acidic cation exchangers connected in series.

Four membrane adsorbers, connected in series, of the Sartobind®-S type (highly acidic cation exchanger with sulfonic acid groups on a cellulose hydrate membrane) from Sartorius-Stedim Biotech GmbH, Order No. S 15x, were used for this purpose. The adsorbers were flushed with 100 ml of a 10 mmol/l citrate buffer (pH=4.0, buffer 1) using a suitable peristaltic pump. 25 ml of the respective reaction mixtures were applied to the adsorbers. The individual fractions of unreacted lysozyme and of mono- and di- or tripegylated lysozyme were eluted by a step gradient from 0 mol/l NaCl in buffer 1 to 1 mol/l NaCl in buffer 1 (corresponds to buffer 2).

The di- or tripegylated lysozyme was isolated in the first step at 15% buffer 2, the monopegylated lysozyme in the second step at 35% buffer 2, and the unreacted lysozyme in the third step at 100% buffer 2.

The fractions isolated in these steps were separated on the basis of their size/molar mass by size-exclusion chromatography on a "G3000 SwXL" column from TOSOH Bioscience, Stuttgart, Germany, by linear elution with an eluent composed of 0.1 mol/l of sodium sulfate and 0.1 mol/l of sodium phosphate (pH=7.0).

Moreover, the fractions were separated by analytical gel electrophoresis in a 12% polyacrylamide gel from ANAMED Deutschland (Order No. TG12112) and in an electrophoresis chamber "Elphor Vario 2" from Bender and Hobein, Heidelberg, Germany. Subsequent staining with barium iodide for detecting polyethylene glycol and subsequent staining with Coomassie Blue for detecting pegylated or nonpegylated proteins confirmed the findings obtained by size-exclusion chromatography.

Analogous reactions were also carried out for polyethylene glycols with a mean molecular weight of 10 000 Da and of 30 000 Da (SUNBRIGHT® Order No. ME-100 AL (batch M999653), SUNBRIGHT® Order No. ME 300 AL (batch M4659)).

After these independent chromatographic and gel-electrophoretic comparative analyses, the purified reaction batches in which 5-kDA, 10-kDa and 30-kDa PEG had been used revealed in each case a mixture of nonpegylated lysozyme and of mono-, di- and tripegylated lysozyme. The batches are subsequently referred to as 5-kDa, 10-kDa and 30-kDa PEG mixture, respectively.

Comparison of various microporous membrane materials with a microporous cellulose acetate membrane for separating the 5-kDa, 10-kDa and 30-kDa PEG mixtures into their individual components.

The equilibration and binding buffer employed (hereinbelow "buffer A") was a buffer of 1 mol/l trisodium citrate (composed of 192.12 g of citric acid from Merck, Darmstadt, adjusted with 1 mol/l NaOH) with a pH of 8.0. The elution buffer used (subsequently "buffer B") was a buffer of 0.1 mol/l trisodium citrate (composed of 19.21 g of citric acid from Merck, Darmstadt, adjusted with 1 mol/l NaOH) with a pH of 8.0. 0.5 ml of the mixture to be separated, of lysozyme and its pegylation products (mono-, di- and tripegylated lysozyme), was applied by means of a suitable sample loop and analyzed in an FPLC system ÄKTAprime® plus from GE Healthcare, USA, as described in Table 2, step 3.

The following microporous membranes were used for the separation of the abovementioned mixtures for comparing their separation efficiency with the microporous cellulose acetate membrane used in the process according to the invention (cf. Table 1).

TABLE 1

| Membrane type from Sartorius Stedim Biotech GmbH | Pore size/μm | Type No. | Batch No. |
|---|---|---|---|
| 1) Cellulose acetate (CA) | 0.45 | 11106 | —100———G |
| 2) Cellulose acetate (CA) | 0.20 | 11107 | —100———G |
| 3) Polyamide (PA) | 0.20 | 25007 | —142———N |
| 4) Polyether sulfone (PESU) | 0.20 | 15407 | ——50———MIN |
| 5) Cellulose nitrate (CN) | 0.45 | 11306 | 142———G |
| 6) Regenerated cellulose (RC) | 0.20 | 18407 | 142———G |
| 7) Sartobind ® S | 3.00 | 94IEXS42-001 | ** |
| 8) Sartobind ® phenyl | 3.00 | * | ** |

\* The membrane used here was taken from a commercially available capsule from Sartorius Stedim Biotech GmbH (Order No. 96HICP42E9BFF) and used as described.
\*\* No batch information available. The products take the form of cellulose hydrate membranes with sulfonic acid ligands (S type) or with phenyl ligands derived from aniline (phenyl type).

In each case three roundels 30 mm in diameter were punched out from the membranes specified in Table 1 and installed in suitable holders. After the membranes had been wetted completely with buffer A, they were integrated into an FPLC chromatography system of the ÄKTAprime® type. This was followed by a manual wash step with buffer A.

An automated program (cf. Table 2) was established for comparing the membranes. Elution was effected using the stated volumes in ml in a decreasing gradient from 100% to 0% buffer A. The elution step was followed by a further wash step with buffer B.

TABLE 2

| Step | Volume/ml | Concentration of buffer B (%) | Sample application |
|---|---|---|---|
| 1 | 0.0 | 0 | — |
| 2 | 5.0 | 0 | — |
| 3 | 5.1 | 0 | sample application |
| 4 | 10.0 | 0 | — |
| 5 | 100.0 | 90 | — |
| 6 | 100.1 | 100 | — |
| 7 | 110.0 | 100 | — |
| 8 | 110.1 | 0 | — |
| 9 | 120 | 0 | — |

In steps 1 to 3, the program carried out a wash step of the installed membrane; in step 3, the analysis sample of lysozyme and its pegylation products was applied simultaneously by using an appropriately switched valve so that the mixture to be analyzed was applied to the membrane. Between steps 4 and 5, a linear gradient between buffers A and B was generated by a suitably controlled proportionating valve. Since buffer B has a lower ion concentration than buffer A, a gradient which is decreasing in respect of the salt content is generated.

The chromatogram peaks were collected in fractions, analyzed by the above-described analytical methods of size exclusion, cation exchange and gel electrophoresis and assigned to the various fractions which contained lysozyme and its pegylation products.

FIGS. 1 to 5 show the chromatograms while carrying out the process according to the invention using the 0.20 μm cellulose acetate membrane mentioned in Table 1 under No. 2). In the figures, L denotes lysozyme, M monopegylated lysozyme, D dipegylated lysozyme and T tripegylated lysozyme.

Figure 2:
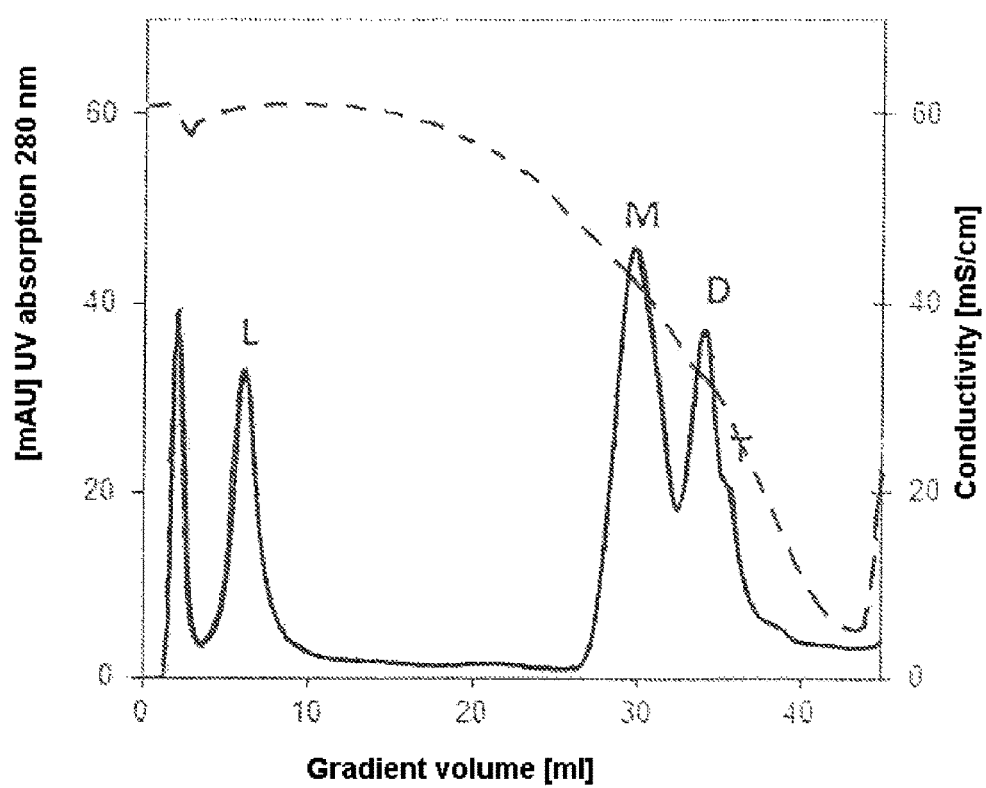
FIG. 2 a chromatogram of a reaction mixture from the reaction of lysozyme with 10-kDa polyethylene glycol during a gradient elution, the volume of the 0.20 μm cellulose acetate membrane being 1 ml.
Figure 3:
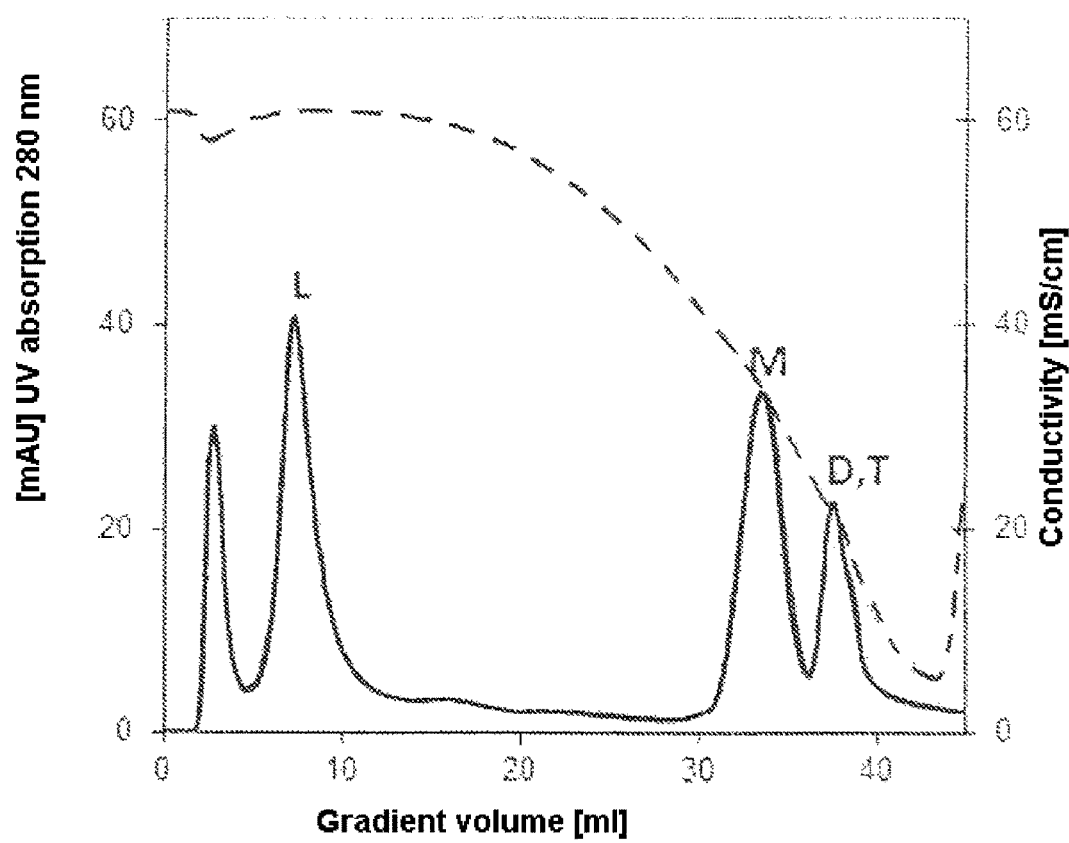
FIG. 3 a chromatogram of a reaction mixture from the reaction of lysozyme with 30-kDa polyethylene glycol with a 1-ml volume of the 0.20 μm cellulose acetate membrane and gradient elution.

According to FIGS. 1 to 3, the course of the separation of the mixtures was monitored by measuring the UV absorption at 280 nm in the adsorber outflow and the eluate conductivity as a function of the duration of the automated program as specified in Table 2, i.e. as a function of the gradient volume, the membrane volume being 1 ml. Elution was carried out in a gradient using the program as specified in Table 2 at a flow rate of 1 ml/min and a gradient length of 30 ml. The course of the conductivity reflects the decrease of the gradient of the salt concentration over time, caused by the simultaneous increase in the amount of buffer B with a lower salt concentration than buffer A.

It can be seen from FIGS. 1 to 3 that nonpegylated lysozyme L and monopegylated lysozyme M can be reliably removed from the mixture of dipegylated lysozyme D and tripegylated lysozyme T.

Figure 4:
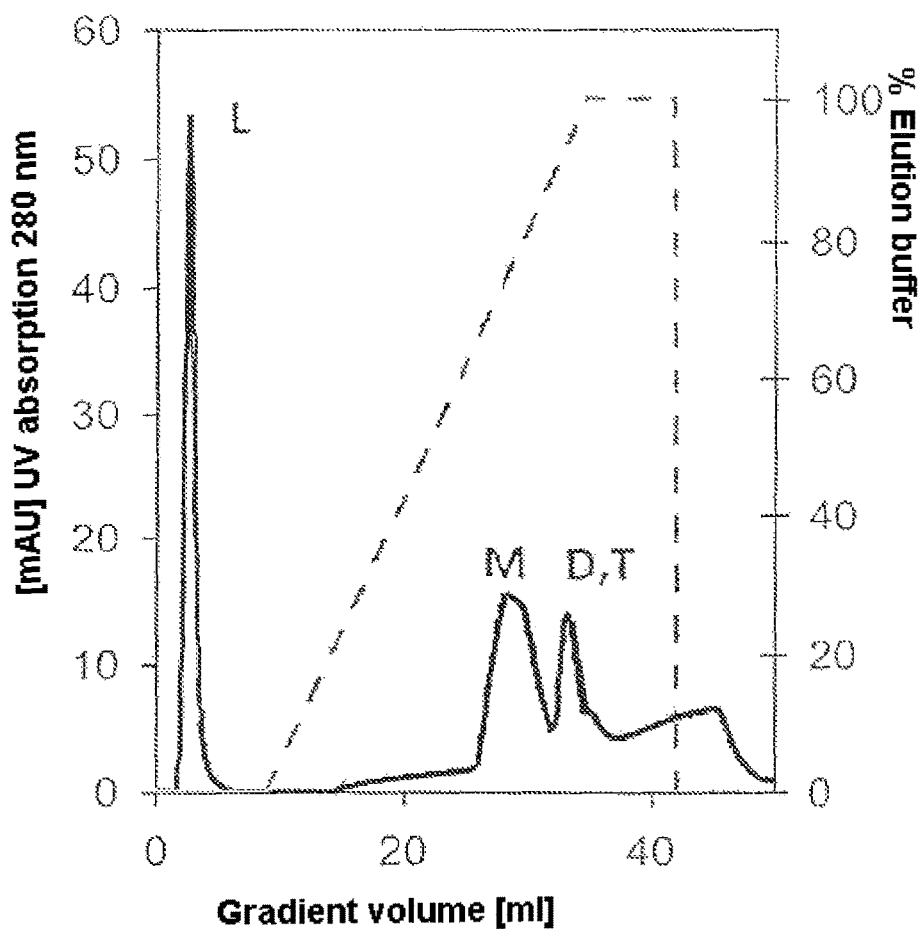
FIG. 4 a chromatogram of the reaction mixture from the reaction of lysozyme with 5-kDa polyethylene glycol during a gradient elution, the volume of the 0.20 μm cellulose acetate membrane being 0.5 ml.
Figure 5:
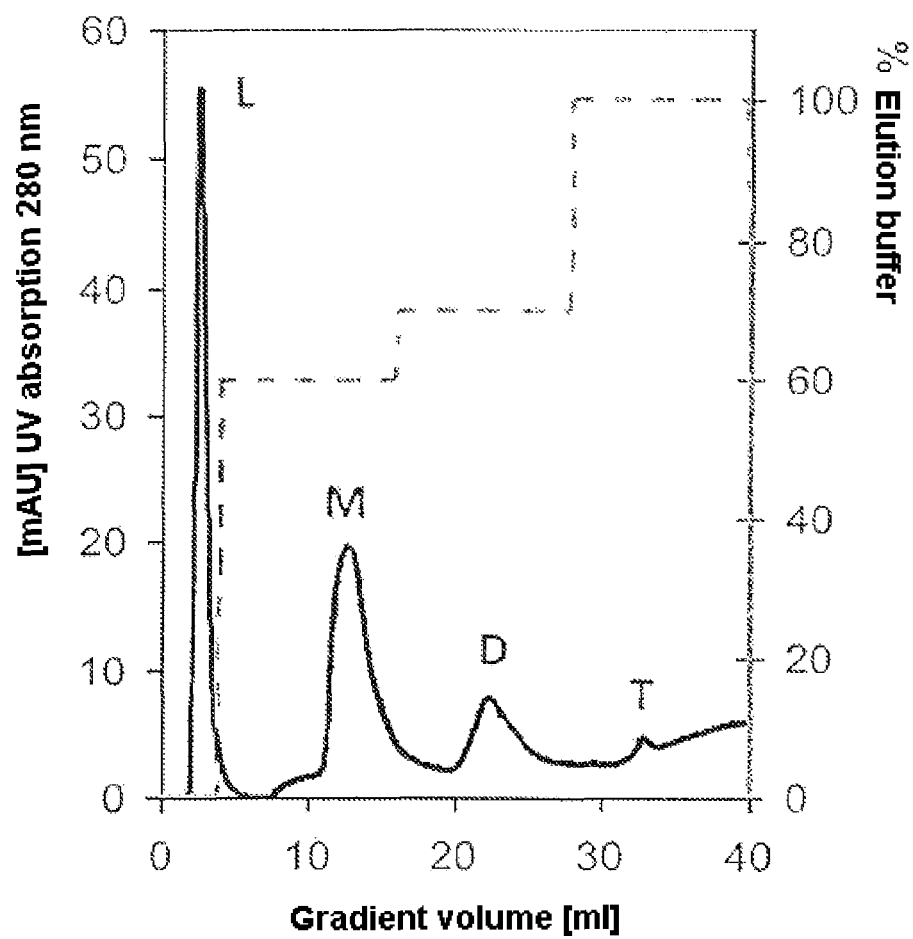
FIG. 5 a chromatogram of the reaction mixture of FIG. 4 in a step elution, the volume of the 0.20 μm cellulose acetate membrane being 0.5 ml.

According to FIGS. 4 and 5, the course of the separation of the 5-kDa PEG mixture into its individual components was monitored as a function of the gradient volume in ml on the basis of the UV absorption at 280 nm and as a function of "% Elution buffer", i.e. the amount of buffer B in the elution solution. Here, the membrane volume amounted to 0.5 ml, with FIG. 4 showing a linear gradient elution while FIG. 5 shows an optimized step elution with three plateaus.

If the substance separation is carried out in the linearly increasing gradient of buffer B shown in FIG. 4, it is possible reliably to remove nonpegylated lysozyme and monopegylated lysozyme from the mixture of di- and tripegylated lysozyme. In contrast to the mixture according to FIG. 1, FIG. 5 shows that it is possible for the 5-kDa reaction mixture not only to remove nonpegylated and monopegylated lysozyme, but also to separate the mixture of di- and tripegylated lysozyme if the optimized step gradient shown in FIG. 5 is set. The buffer used in this context was a 1.7-molar potassium phosphate buffer with a pH of 8.6. The flow rate was 10 ml/min and the gradient length 30 ml. The three steps of the gradient were in each case 60%, 70%, and 100% (in each case 13 ml) of buffer B.

The step elution gradient according to FIG. 5 permits the complete separation of a mixture of lysozyme and its mono-, di- and tripegylated reaction products into the individual components.

With reference to the chromatogram of FIG. 5, it is furthermore possible, owing to the base line separations achieved, to quantitatively determine the individual amounts of unreacted lysozyme and its mono-, di- and tripegylated derivatives present in the reaction mixture, which is done by integration of the individual peak areas and comparison with the respective reference substances.

Comparative experiments under analogous conditions were also carried out for the other membrane materials 3) to 8) of Table 1. The results are shown in Table 3.

TABLE 3

| Membrane type (cf. Table 1) | Binding capacity for lysozyme | Binding capacity for pegylation products |
| --- | --- | --- |
| 1) Cellulose acetate (CA) | 0 | +/+ |
| 2) Cellulose acetate (CA) | 0 | +/+ |
| 3) Polyamide (PA) | +/− | +/+ |
| 4) Polyether sulfone (PESU) | 0 | 0 |
| 5) Cellulose nitrate (CN) | +/− | +/− |
| 6) Regenerated cellulose (RC) | 0 | 0 |
| 7) Sartobind® S | 0 | 0 |
| 8) Sartobind® phenyl | +/− | +/+ |

The symbol "0" means that the respective component is not adsorbed onto the membrane material tested. A plus sign before the forward slash means binding to the membrane material, a plus sign after the forward slash means that the components can be eluted from the membrane material. A minus sign after the forward slash means that the respective component cannot be eluted from the membrane material. It can be seen from Table 3 that no binding of the nonpegylated lysozyme is observed exclusively for the two cellulose acetate membranes 1) and 2), but that the pegylation products of the lysozyme can be eluted from the membranes when the ion concentration is lowered. The cellulose acetate membranes 1) and 2) have a breakthrough capacity for monopegylated lysozyme (based on the 5-kDa polyethylene glycol with which lysozyme has been reacted) of 0.042 mg/cm$^2$ corresponding to 1.7 mg of monopegylated lysozyme per ml membrane volume. In all the other tested membranes 4), 6) and 7), either no binding of the components studied was observed, or else the nonpegylated lysozyme was adsorbed, but could subsequently not be desorbed (cf. membranes 3), 5) and 8)).

A further advantage of the process according to the invention is the savings that can be realized when reusing the inexpensive cellulose acetate membrane material for subsequent separation operations.

The invention claimed is:

1. A process for separating a mixture of a protein and its polyalkylene glycol-reaction product, comprising:
   providing a mixture comprising the protein and the polyalkylene glycol-reaction product in a fluid,
   contacting the mixture with a microporous cellulose acetate membrane, thereby binding the polyalkylene glycol-reaction product to the cellulose acetate membrane, wherein the protein does not bind to the cellulose acetate membrane,
   separating the protein from the polyalkylene glycol-reaction product containing cellulose acetate membrane, and then
   desorbing the polyalkylene glycol-reaction product from the cellulose acetate membrane,
   wherein the polyalkylene glycol-reaction product is selected from the group comprising a mono-polyalkylene glycol-functionalized protein, a poly-polyalkylene glycol-functionalized protein, or mixtures thereof.

2. The process of claim 1, wherein the polyalkylene glycol is a polyethylene glycol with a mean molecular weight of from 5 to 30 kDa.

3. The process of claim 1, wherein the polyalkylene glycol-reaction product is a mixture of a mono-polyalkylene glycol-functionalized protein and a poly-polyalkylene glycol-functionalized protein, and wherein the polyalkylene-glycol-functionalized proteins are desorbed from the cellulose acetate membrane in order based on the number of polyalkylene glycol-functionalizations.

4. The process of claim 3, wherein the cellulose acetate membrane is composed of cellulose monoacetate, cellulose diacetate, cellulose triacetate or mixtures of these.

5. The process of claim 4, wherein the pore size of the cellulose acetate membrane is between 0.1 and 15 μm.

6. The process of claim 1, wherein the protein is selected from the group comprising immunoglobulins, insulins, interferons, albumins such as lactalbumin, ovalbumin, bovine serum albumin, myelopoietin, erythropoietin, trichosanthin, tumor necrosis factors or enzymes such as methioninase, ribonucleases, staphylokinases or lysozyme, or monoclonal or recombinant antibodies.

7. The process of claim 6, wherein the protein is lysozyme and the reaction product is a mixture composed of lysozyme which is mono-, di- and trifunctionalized by polyethylene glycol.

8. The process of claim 3, wherein the polyalkyleneglycol-functionalized proteins are desorbed with an aqueous solution of a salt selected from an inorganic ammonium, alkali metal or alkaline earth metal salt, and/or of an ammonium, alkali metal or alkaline earth metal carboxylate, dicarboxylate, or tricarboxylate.

9. The process of claim 8, wherein the polyalkylene glycol functionalized proteins are desorbed in order of PEGylation.

10. The process of claim 9, wherein the polyalkylene glycol functionalized proteins are desorbed in a gradient elution with increasing concentration of the salt.

11. The process of claim 9, wherein the polyalkylene glycol functionalized proteins are desorbed in a step elution with increasing concentration of the salt.

* * * * *